(12) United States Patent
Averbuch

(10) Patent No.: US 9,278,203 B2
(45) Date of Patent: Mar. 8, 2016

(54) CT-ENHANCED FLUOROSCOPY

(75) Inventor: Dorian Averbuch, Ramat HaSharon (IL)

(73) Assignee: Covidien LP, Mansfield, MA (US)

( * ) Notice: Subject to any disclaimer, the term of this patent is extended or adjusted under 35 U.S.C. 154(b) by 1703 days.

(21) Appl. No.: 12/056,123

(22) Filed: Mar. 26, 2008

(65) Prior Publication Data

US 2008/0262342 A1    Oct. 23, 2008

Related U.S. Application Data

(60) Provisional application No. 60/908,126, filed on Mar. 26, 2007.

(51) Int. Cl.
| | |
|---|---|
| A61B 5/05 | (2006.01) |
| A61M 31/00 | (2006.01) |
| A61B 6/12 | (2006.01) |
| A61B 6/00 | (2006.01) |
| A61M 25/00 | (2006.01) |
| A61M 25/01 | (2006.01) |
| A61M 25/06 | (2006.01) |

(52) U.S. Cl.
CPC .............. *A61M 31/005* (2013.01); *A61B 6/12* (2013.01); *A61B 6/487* (2013.01); *A61B 6/5235* (2013.01); *A61B 6/481* (2013.01); *A61M 25/0045* (2013.01); *A61M 25/0082* (2013.01); *A61M 25/0108* (2013.01); *A61M 2025/0096* (2013.01); *A61M 2025/0681* (2013.01)

(58) Field of Classification Search
USPC .................................................. 600/424, 427
See application file for complete search history.

(56) References Cited

U.S. PATENT DOCUMENTS

| | | | |
|---|---|---|---|
| 4,587,975 A * | 5/1986 | Salo et al. ..................... | 600/506 |
| 4,593,687 A | 6/1986 | Gray et al. | |
| 5,419,324 A | 5/1995 | Dillow | |
| 6,028,912 A | 2/2000 | Navab | |
| 6,351,513 B1 * | 2/2002 | Bani-Hashemi et al. ......... | 378/8 |
| 6,389,104 B1 | 5/2002 | Bani-Hashemi et al. | |
| 6,520,934 B1 * | 2/2003 | Lee et al. ................... | 604/103.1 |
| 7,033,325 B1 | 4/2006 | Sullivan | |
| 7,505,809 B2 * | 3/2009 | Strommer et al. ............ | 600/424 |

(Continued)

OTHER PUBLICATIONS

ISA/US, Search Report and Written Opinion, International Application No. PCT/IB08/02163, Mar. 25, 2009, 7 pages.

(Continued)

*Primary Examiner* — Long V Le
*Assistant Examiner* — Ellsworth Weatherby

(57) ABSTRACT

Real-time, enhanced imaging of remote areas, too minute for CT imaging, is made possible through a probe having a radiopaque tip as well as radiopaque volume markers. When deployed, the markers outline the space containing the tip such that both the tip and the volume containing the tip are viewable on a fluoroscope. This device may be used in conjunction with or independently of 3-D volumes created from CT scans and 3-D tip sensors.

11 Claims, 5 Drawing Sheets

(56) References Cited

U.S. PATENT DOCUMENTS

| | | | |
|---|---|---|---|
| 2002/0143324 A1* | 10/2002 | Edwards | 606/41 |
| 2003/0088179 A1 | 5/2003 | Seeley et al. | |
| 2003/0220555 A1 | 11/2003 | Heigl et al. | |
| 2004/0143317 A1 | 7/2004 | Stinson et al. | |
| 2005/0004454 A1* | 1/2005 | Mitschke et al. | 600/427 |
| 2005/0027193 A1* | 2/2005 | Mitschke et al. | 600/427 |
| 2005/0215874 A1* | 9/2005 | Wang et al. | 600/407 |
| 2006/0023840 A1* | 2/2006 | Boese | 378/98.12 |
| 2006/0079759 A1 | 4/2006 | Vaillant et al. | |
| 2006/0116575 A1 | 6/2006 | Willis | |
| 2007/0232898 A1* | 10/2007 | Huynh et al. | 600/424 |

OTHER PUBLICATIONS

European Search Report for corresponding application No. 08789104.0, dated Apr. 24, 2015.

\* cited by examiner

CT-ENHANCED FLUOROSCOPY

RELATED APPLICATIONS

This application claims priority to U.S. Provisional Application Ser. No. 60/908,126 filed Mar. 26, 2007 entitled CT-Enhanced Fluoroscopy which is hereby incorporated by reference.

BACKGROUND OF THE INVENTION

The various inventions disclosed herein relate generally to the superimposed presentation of relatively low-resolution or low-quality images, acquired in real time, onto relatively high-resolution or high-quality images acquired preoperatively.

Conventional fluoroscopy is widely used during medical procedures as a visualization and validation imaging tool for guiding medical instruments inside the human body. Although medical instruments like catheters, biopsy tools, etc., are clearly visible on a fluoroscopic picture, organic features such as soft tissue, blood vessels, suspicious tumor lesions etc., are quite transparent and hard to identify with conventional fluoroscopy. As such, frequently a higher quality diagnostic image is acquired, such as CT scan, prior to the operation.

Before a biopsy or therapeutic procedure, a physician studies the patient's CT scan and identifies the target area, such as an area containing a suspicious lesion. Based on his or her professional knowledge, the physician intuitively plans the upcoming procedure by estimating and memorizing the lesion's size, shape and location inside the soft tissue of the chest or abdomen.

Next a procedure is performed, such as a biopsy, which involves the introduction of a medical instrument into the target area. During the procedure, a fluoroscopic picture is used by physician to aid the maneuvering of medical instruments inside the soft tissue towards the target area. The medical instrument is clearly visible but the tissue is transparent.

Hence, the current method has the following disadvantages:

1) When performing diagnostics of suspicious area, a common practice is to use multiple biopsies to increase the diagnostic success probability. This technique increases the procedure time and radiation exposure time, thereby increasing the risk to the patient and attending personal of potential X-ray exposure-related issues.
2) The existing method is inaccurate in locating the position of the medical instrument relative to the lesion because:
   a. Information regarding lesion location and size, such as that potentially available from a CT image, are not utilized by the diagnostic and therapeutic procedures that are performed under a fluoroscope.
   b. The targeted tissue is rarely seen on a fluoroscopic image.
   c. The fluoroscopic image is designed for visual perception and not intended to provide accurate, measurable information.
   d. A fluoroscopic image is two-dimensional, while an internal lesion is located in three-dimensional space.
3) There is a potential risk of excessive bleeding or pneumothorax following biopsy, caused by implement injuries to internal organs or blood vessels not seen by the fluoroscope.
4) Internal organs and other tissues move due to breathing, heart activity, etc. Because these features are transparent to a fluoroscope, it is difficult or impossible to be sure that the path of a medical instrument remains as planned toward the targeted area by monitoring a fluoroscope alone. Observing external body movement does not always provide an accurate indication of internal organ movement.

Moreover both due to the limited CT resolution and low radio-opacity of the bronchial tissue the peripheral bronchial airways are not likely to be seen using CT, especially when using a low-dose CT, which is much more commonly used, less expensive, and safer for the patient than a high-dose CT. However when targeting the small peripheral lesions it is essential to identify and utilize the path leading to peripheral lesion.

These inaccuracies result in a low diagnostic success rate and, therefore, such procedures are usually reserved for larger lesions.

One aspect of the present invention is to provide a method that improves upon conventional bronchoscopy procedures, whether using existing medical equipment or the apparatus of the present invention.

Another aspect of the present invention is to provide a method that improves upon conventional biopsy or therapeutic procedures in organs that are not seen under fluoroscopy, whether using existing medical equipment or the apparatus of the present invention.

The proposed method improves the quality of fluoroscopic imaging to an extent that allows fluoroscopic imaging to be used as an accurate measuring modality. Hence, the non- or minimally-invasive and inexpensive attributes of fluoroscopic imaging procedures are utilized. The proposed method is mostly suitable to assist the diagnostic and therapeutic procedures in the lungs, liver and kidney.

One aspect of an embodiment of the present invention navigates a medical instrument to a targeted anatomy extracted from high-quality volume data.

Another aspect of an embodiment of the present invention provides a real-time image of a static or moving medical instrument and a targeted anatomical feature in proximity thereto.

Yet another aspect of an embodiment of the present invention provides a method and apparatus that combines single or multiple 2D fluoroscopic images with previously acquired high-quality volume data.

Another aspect of an embodiment of the present invention provides a method and apparatus that dynamically determines the most visually informative combination of single or multiple 2D fluoroscopic images with previously acquired high-quality volume data on an application-specific or user-specified basis.

One aspect of the present invention provides various embodiments of catheters and endoscopes that allow 3D shape data to be determined from single or multiple 2D fluoroscopic images.

Another aspect of an embodiment of the present invention provides an apparatus and method for maintaining an accurate registration between a dynamic fluoroscopic image and a static CT image.

Additional aspect of this invention present the way of local improvement to the anatomy extracted from high-quality volume data of limited resolution.

Yet another aspect of the invention provides a technique for improving the coverage area of a low-dose CT scan, such that a high-dose CT scan can be avoided.

DETAILED DESCRIPTION OF THE INVENTION

Figure 1:
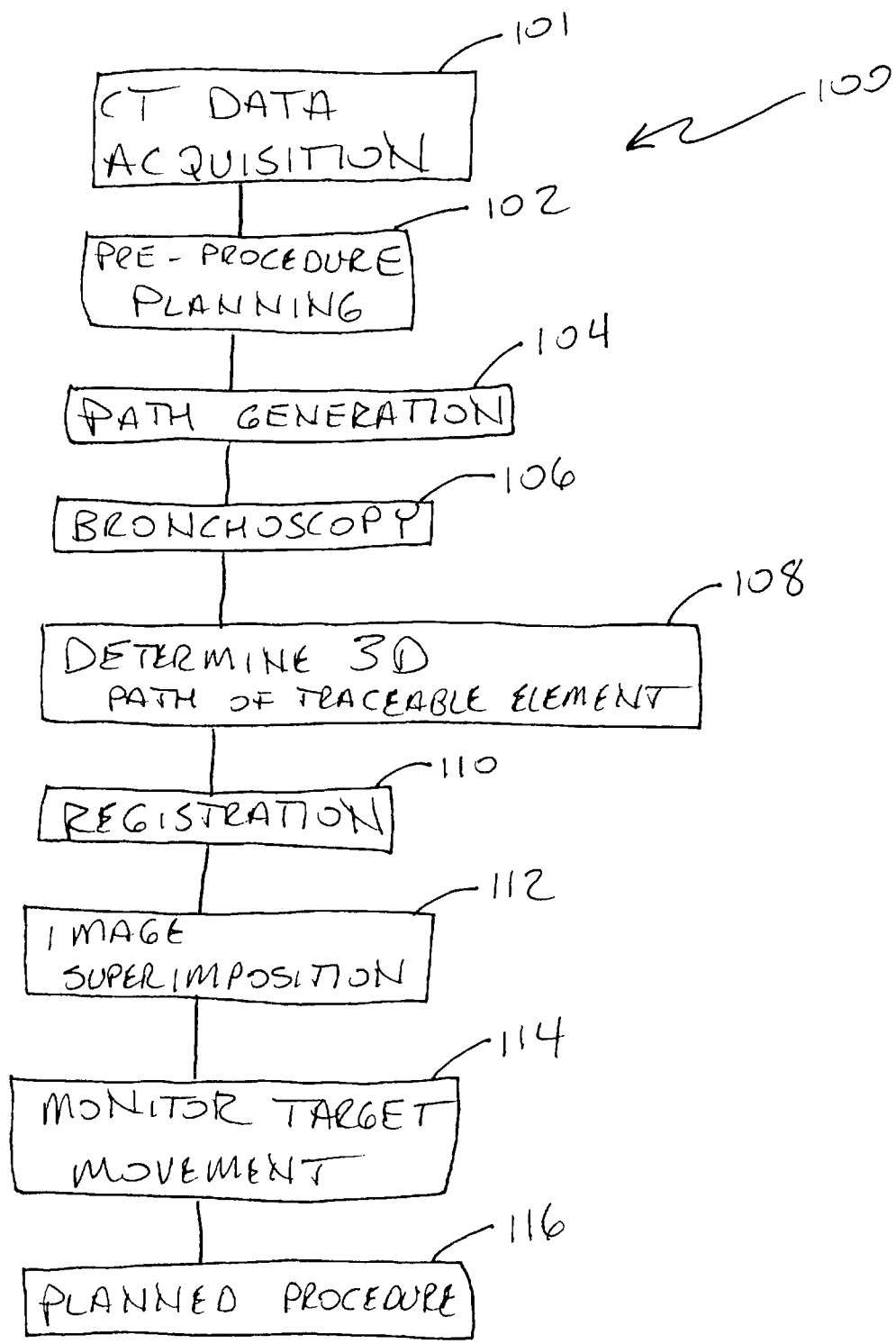
FIG. 1 is a flowchart of a method of the present invention.

Referring now to FIG. 1, there is shown a flowchart that illustrates a method 100 of the present invention.

At 101 of the method 100, CT data is acquired and transformed into a 3D CT volume, which will be used during the procedure in combination with the real-time X-ray (e.g., fluoroscopic) data. This CT data may even be low-dose CT that is later enhanced with fluoroscopic data, if necessary. Enhancement with fluoroscopic data will be explained in more detail below.

At 102 of the method 100, the practitioner, such as a physiologist for example, performs pre-procedure planning on the CT data acquired at 101, during which he or she marks each point of interest (e.g., a suspicious lesion) and its dimensions. This procedure may be performed manually or semi-automatically, such as when the points of interest are automatically identified by computer software.

Once the point of interest is marked, at 104 the recommended path to the point of interest area inside the lungs is created and stored, preferably automatically. Optionally, guidance instructions based on anatomic knowledge are automatically created and presented to the user. The guidance instructions will direct the user to a sequential plurality of turning points. Each turning point is chosen to direct the tip of the inserted instrument in a predefined direction prior to bronchoscope insertion.

The bronchoscopy is performed at 106. The bronchoscope has at least one traceable portion or a general traceable quality, making the bronchoscope a traceable element. This may be accomplished by forming the bronchoscope from a traceable material or adding one or more traceable markers to the bronchoscope. Traceable elements are not limited to bronchoscopes. For example, traceable elements may be constructed as stand-alone devices or formed by adding a traceable quality to catheters, guidewires, needles, extended working channels, tubes, or any other device inserted into a body cavity. The traceable element is easily viewed on a fluoroscope (or any type of X-ray imaging device) and designed to be tracked through the limited number of fluoroscopic pictures or image planes. This technique enables a three-dimensional path of the instrument inside the human body to be determined at 108. Each fluoroscopic picture will be calibrated using one of the well known calibration techniques, prior to the registration.

Next, at 110, the fluoroscopic image is registered to the CT volume from 101 The co-registration between the fluoroscopic image and CT volume is preferably performed in 2 steps:

First, an initial estimation is made regarding the position and orientation of the fluoroscopic image plane using either internal anatomical structures clearly identified by fluoroscopic and CT images (for example bones) or externally attached radiopaque elements. Notably, it is not required to attach external radiopaque elements to the patient during the CT scan.

Second, an accurate registration is performed by comparing the three-dimensional path of the instrument determined at 108 with the three-dimensional anatomic path (airways) inside the "virtual lungs" of the CT volume. If the three-dimensional path of the instrument is long enough, it will likely only match one correspondingly-shaped anatomic path. Because it is known that the traceable element remains within the airways, its precise location in the lungs can be determined by comparing its shape with a model of the patient's airways. Each adjunctive anatomic path will be calculated with the suitable cost-effective weight function, as a most probable one from the few existing options.

Once registered, at 112 the fluoroscopic image may be superimposed onto or under the CT image and fused therewith.

Optionally, image accuracy is enhanced at 114. Because the CT image is static, but the fluoroscopic image is occurring in real-time, the fluoroscopic image shows movement. However, because soft tissues are not displayed on a fluoroscopy, a tracing element, in addition to the traceable characteristic of the catheter, is utilized to enable the tracing of internal soft tissue movement in the proximity of the point of interest. The tracing element may comprise a plurality of temporary or permanently implanted markers implanted around the target area to provide a real-time outline of the position of the target area as the patient breathes. One embodiment provides a very flexible radiopaque string-like element that lays flat against the tissue when released from the catheter. In one embodiment, this tracing element resembles a fine chain, attached at its distal end to the distal end of a catheter ("catheter" is being used herein in a general sense to include any and all devices that are threaded through the anatomic path to the target area, including but not limited to, bronchoscopes, probes, guidewires, tubes, etc.) and otherwise remaining on the outside of the catheter such that it is dragged to the target location with the catheter. If appropriate, a release mechanism detaches the tracing element from the distal end of the catheter, allowing gravity to pull the tracing element downward to rest along the contours of the airway. This radiopaque traceable element may additionally be used at step 108 to provide an even more detailed 3D anatomic path shape than CT could provide, due either to its limited resolution or because of the low radiopacity of bronchial airway tissue. Hence, the image of the local anatomy of the bronchial airways is improved with the help of fluoroscopic imaging. Alternatively, the distal end of the tracing element may remain attached to an external portion of the catheter, in cases where the final "leg" of the path is uphill, to prevent the tracing element from falling away from the target. One embodiment, explained below, provides a radiopaque spray that can similarly be used to enhance the CT volume with fluoroscopic data.

Once the traceable element is in place, the user is able to perform the planned procedure at 116 under the X-ray fluoroscopy in the proximity of the traceable element, taking the advantage of the accuracy of the CT data to measure the spatial location of an instrument relative to the target area, regardless of whether the target area is seen by fluoroscopy.

Figure 2:
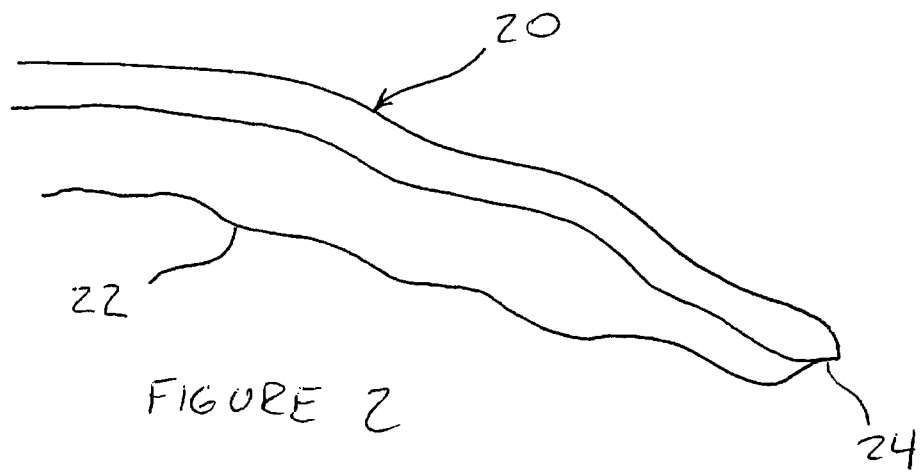
FIG. 2 is perspective view of an embodiment of a traceable element of the present invention; and,
FIG. 3 is perspective view of an embodiment of a catheter with a traceable element of the present invention.
Figure 3:
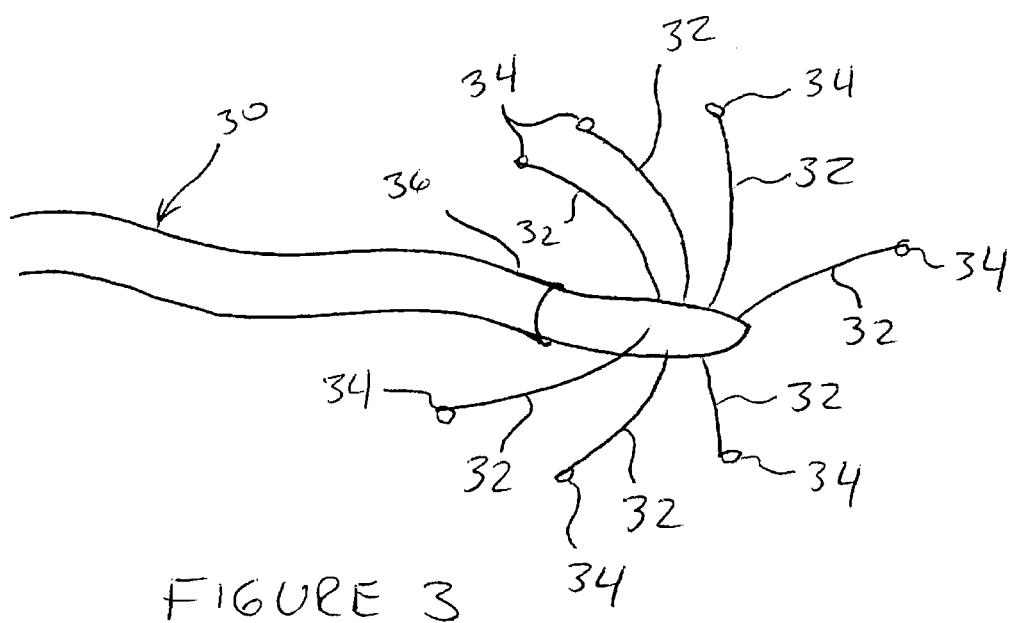

Having explained various embodiments of the method of the present invention, several structural features are now described. Various embodiments of non-implantable tracing elements are shown in FIGS. 2 through 9. FIG. 2 shows a catheter 20 and a string-like tracing element 22 attached at the distal end 24 of the catheter 20. FIG. 3 shows a catheter 30 with a plurality of spring-like "whiskers" 34 extending therefrom, each having a marker 34 at its distal end. The whiskers 34 are held under a sheath 36 until the target is reached. At that point the sheath 36 is retracted and the whiskers 32 radiate until the markers 34 contact surrounding tissue. Hence, the radiopaque markers 34 provide a trace of a three dimensional volume surrounding the target area.

Figure 4:
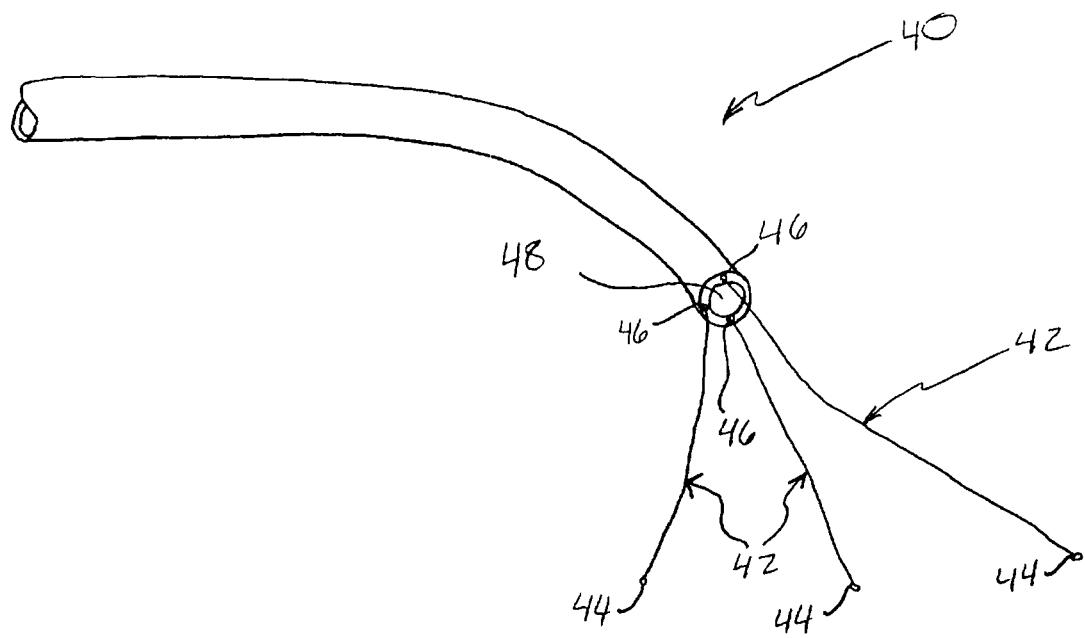
FIG. 4 is a perspective view of an embodiment of a catheter with a traceable element of the present invention.

FIG. 4 shows a catheter 40 with a plurality of retractable tracing elements 42. The tracing elements 42 include markers 44 at their distal tips. Once the distal tip of the catheter 40 has reached the target location, the tracing elements 42 are extended through one or more small channels 46 running through the sidewall of the catheter 40. The catheter 40 has a center lumen 48 that remains open to accommodate a scope or act as a working channel for the introduction of tools. The markers 44 are extended until they contact tissue. They are then used to track the movement of the tissue and allow the fluoroscopic image to be fused to the CT volume such that it moves therewith, and gives the appearance that neither image is moving. Though it is shown that each tracing element extends through an individual, dedicated 46, it will be apparent to one skilled in the art that, if more than one tracing element 42 is optionally provided, they may share a common channel 46.

Figure 5:
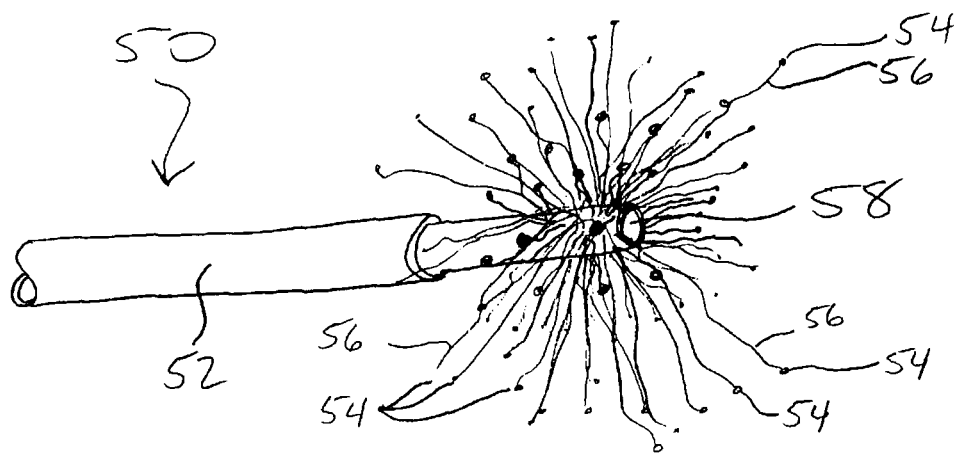
FIG. 5 is a perspective view of an embodiment of a catheter with a traceable element of the present invention.

FIG. 5 shows a catheter 50 with a sheath 52 that can be retracted to release a great many markers 54 each attached to a fine, hair-like element 56. Similar to the embodiment shown in FIG. 3, these markers 54 show the shape of a volumetric space on the fluoroscope. Because there are so many markers 54, they give an accurate view of the shape of the cavity in which they are released. This image can then be matched to a corresponding cavity on the CT volume, using a shape-matching program, and then used to fuse the CT volume to the fluoroscopic image. The markers 54 may also be used without a CT volume in cases where the target site is too remote to show up on a CT volume. The catheter 50 also includes center lumen 58 through which various instruments may be introduced into the cavity.

Figure 6:
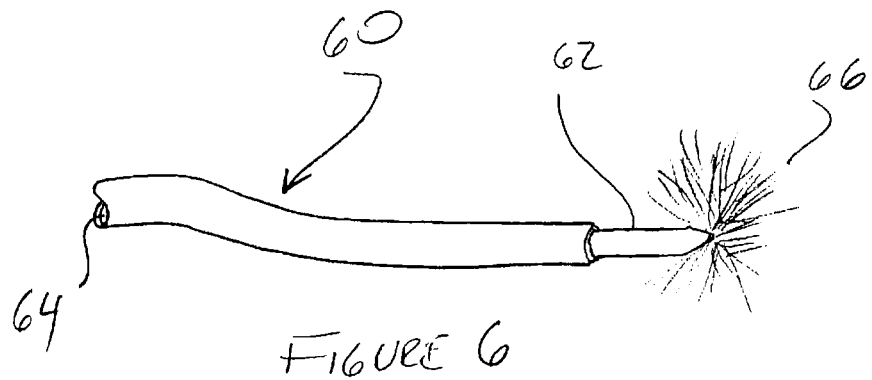
FIG. 6 is a perspective view of an embodiment of a catheter with a traceable element of the present invention.

FIG. 6 shows a catheter 60 that is also useful for illuminating a remote cavity that, for whatever reason (e.g., too small, low radiopacity, outside the CT volume space, etc.) is not viewable on the CT volume or may be used for shape-matching registration to a CT volume as described above. The catheter 60 includes a nozzle device 62 that is insertable through the central lumen 64 of the catheter 60. The nozzle device 62 is used to spray a bio-absorbable imaging agent that fills the airspace in the lung cavity and may also land on the inside surfaces of the lung cavity. The imaging agent may be any imaging agent. Non-limiting examples include radiopaque agents and ultrasonic imaging agents.

It is envisioned that the catheter 60 may be optimally used when navigating to the useful edge of the CT volume and the targeted area has not yet been reached. A small spray of contrast agent is ejected from the nozzle device 62, thereby illuminating a portion of the airway such that it is viewable on the fluoroscope. Not only does the spray allow a space to be seen on an X-ray imaging device such as a fluoroscope, but the image taken of the contrast-agent-enhanced area using the fluoroscope may be used to update the CT volume. Thus, the spray may be used with the fluoroscope to acquire more data to add onto, or grow, the CT volume.

Figure 6A:
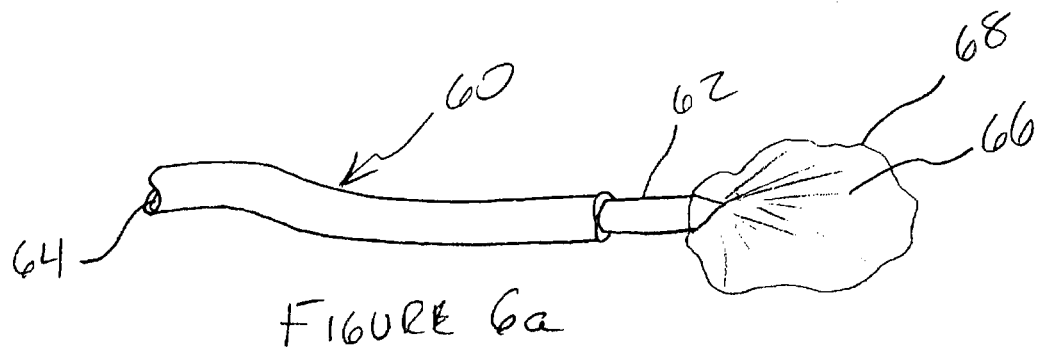
FIG. 6a is a perspective view of an embodiment of a catheter with a traceable element of the present invention.

If it is desirable to collect and remove the contrast spray 66 after the procedure, a catheter 60, such as that shown in FIG. 6a, further equipped with a very flexible, easily conformable sac 68, may be used. The sac 68 is balloon-like in that it expands when the spray is introduced into the sac 68. However, the sac 68 preferably lacks the elasticity of a balloon, such that it does not tend to force the spray 66 out of the balloon when the pressure is released. This way, the sac 68 may inflated with very little pressure and places very little force on the walls of the lung cavity. Once the procedure is completed, negative pressure may be applied to the contents of the sac 68 using the syringe, to remove a portion of the spray 66. The sac 68 and the remaining contents thereof are then removed when the procedure is complete, leaving a clean lung cavity.

Notably, the applicability of the catheter 60 with the spray capacity may be used at any known location in the lungs to enhance the visibility of a given area. Hence, the catheter 60 is compatible with any lung procedure, not just those using the CT-fluoroscopic registration techniques described herein.

Figure 9:
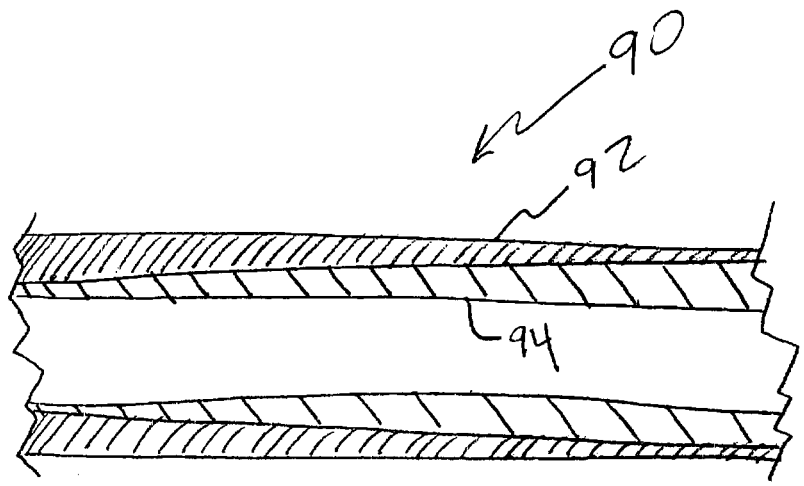

FIGS. 7-9 show various embodiments of catheters that have radiopacic features that enable a three-dimensional profile of the catheter to be calculated from a single, two-dimensional image. These catheters obviate the need for further images to be taken to determine their three-dimensional profiles.

Figure 7A:
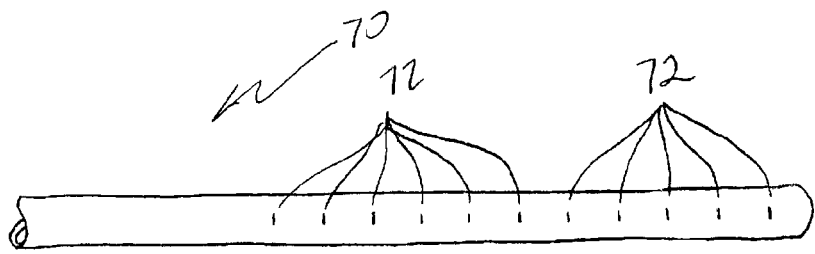
FIGS. 7a-7b are perspective views of an embodiment of a catheter with a traceable element of the present invention.
Figure 7B:
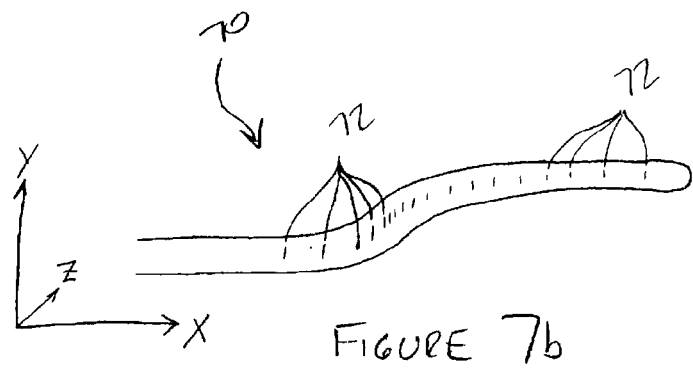

FIGS. 7a and 7b show a catheter 70 having radiopaque markings 72 equally spaced at the distal end of the catheter 70. These markings 72 may be used to measure features inside a body cavity during a procedure. The markings 72 may also be useful in addressing a problem with visualizing a three-dimensional object on a two-dimensional fluoroscopic image. Namely, a two-dimensional fluoroscopic image can be said to show an x-axis and a y-axis. The z-axis is not visible because it comes straight out of the image at the viewer. Hence, objects that have components traveling along the z-axis appear distorted on a fluoroscopic image and it is difficult to tell if the distorted portion is due to a feature that has a z-axis component that is coming out of the image toward the viewer (positive value, for instance) or a z-axis component that is going into the image away from the viewer (negative value).

By providing markings 72, it becomes evident that a section of the catheter 70 has a z-axis component because the markings 72 appear to be closer together. As for whether this z-axis component is positive or negative, information may be taken from the approximate position of the catheter 70 against the CT volume to determine whether a positive or negative z-axis component is more feasible.

Figure 8A:
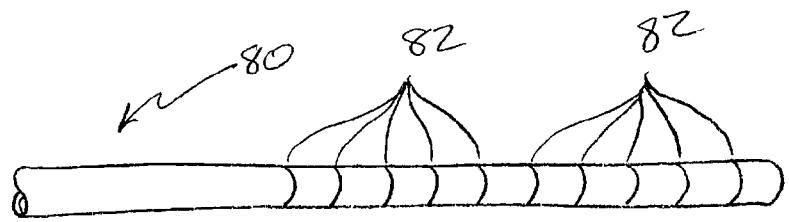
FIGS. 8a-8b are perspective views of an embodiment of a catheter with a traceable element of the present invention; and, FIG. 9 is a cross-sectional elevation of an embodiment of a catheter with a traceable element of the present invention.
Figure 8B:
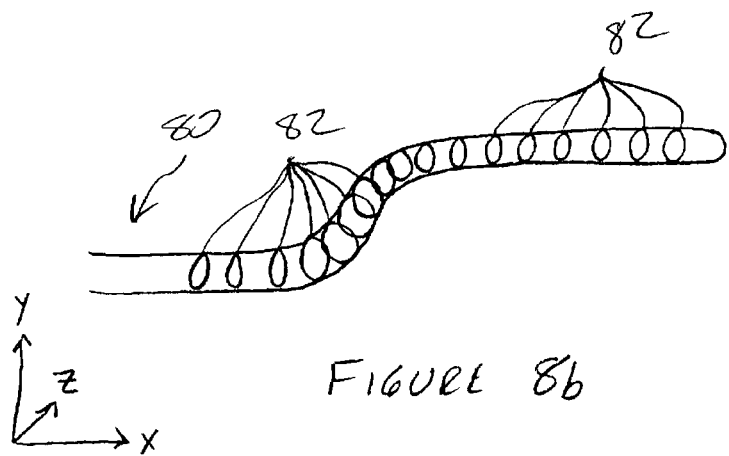

FIGS. 8a and 8b show a catheter 80 having radiopaque rings 82. The rings 82 serve the same function as the markers 72 of FIGS. 7a and 7b. The rings 82 may, however, be easier to see and to visualize than the markers 72.

An examination of not only the two-dimensional shape of a catheter appearing in a two-dimensional X-ray image (such as a fluoroscope image) but also a profile of the radiopacity of the catheter, may also be used to calculate the z-axis features of the catheter's orientation. Taking a single X-ray projection from a known position will yield a 2-dimensional profile of the catheter and a radiopacic profile of the catheter. By comparing the imaged radiopacic profile against the known designed radiopacic profile along the length of the catheter, the z-axis component may be calculated.

Though this method of determining a z-axis component may be accomplished using any catheter having a uniform radiopacity, providing a catheter having a varying radiopaque profile, such as catheter 90 in FIG. 9, may enhance the method. Catheter 90 includes a radiopaque layer 92 surrounding a non-radiopaque layer 94. The thickness of the layer 92 increases while the thickness of the layer 94 correspondingly decreases such that catheter 90 has a uniform sidewall thickness. One skilled in the art will understand that there are other ways to provide a catheter having a varying radiopacic profile. For example, a radiopaque braided layer may surround a catheter that includes areas of varying braid densities. Additionally, the radiopaque layer 92 would work just as effectively if it were surrounded by, rather than surrounding, non-radiopaque layer 94.

Having described several embodiments of markers, traceable elements, sprays, and the like, one skilled in the art will understand that the various embodiments described herein each have unique advantages, and may be used alone or in any combination with each other to best utilize these advantages. Hence, a plurality of tools is provided for use by the practitioner, and the order or combination in which these tools are used are contemplated and considered a part of the present invention, though not necessarily explicated described herein.

The following are the several examples of applications where the CT enhanced fluoroscopy may be utilized.

Sample Application 1

Performing non-invasive diagnostics or treatment of lung cancer. A traceable tube or a traceable Bronchoscope is used for this procedure. Automatically generated guidance instructions may be optionally used. Once the edge of the tube reaches the point of interest area, the biopsy instrument or radiation probe can be inserted through the tube.

Sample Application 2

Performing the diagnostics of liver disorder, cirrhosis, cancer, etc. The traceable catheter, with or without additional tracing elements, is used for this procedure. This is optionally done using an external fine biopsy needle under CT or ultrasound guidance. Using current invention, this procedure may be successfully performed under X-ray fluoroscopy.

Sample Application 3

Needle aspiration biopsy of lungs or kidney. A traceable catheter, with or without additional tracing elements, is used for this procedure. Using the current invention, this procedure may be successfully performed under X-ray fluoroscopy.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of navigating a device to an area of interest and imaging the area of interest in a branched structure comprising:
    using a first imaging modality to obtain at least one image of the branched structure;
    generating a recommended path inside the branched structure to the area of interest;
    imaging at least one tracing element projecting from a device in the branched structure using a second imaging modality, the at least one tracing element able to move with biological movement of the branched structure;
    deploying additional tracing elements to fluoroscopically illuminate locations of anatomical features by releasing a plurality of markers tethered to and radially extending from the device;
    tracing an actual three-dimensional path traveled by the device and the additional tracing elements by acquiring a plurality of images using the second imaging modality;
    registering at least one image from the first imaging modality to at least one image from the second imaging modality by comparing the actual three-dimensional path of the device with the recommended path;
    superimposing the at least one image from the first imaging modality and the at least one image from the second imaging modality; and
    navigating the device through the branched structure to the area of interest by viewing a location of the device in a real-time image obtained with the second imaging modality of the tracing element relative to the at least one image from the first imaging modality.

2. The method of claim 1 wherein using a first imaging modality to obtain an image of the branched structure comprises using CT to obtain at least one image of the branched structure.

3. The method of claim 2 wherein using CT to obtain at least one image of the branched structure comprises using CT to obtain at least one image of the branched structure prior to navigating the device through the branched structure.

4. The method of claim 2 wherein using CT to obtain at least one image of the branched structure comprises using CT to obtain a plurality of images of the branched structure.

5. The method of claim 4 wherein using a first imaging modality to obtain at least one image of the branched structure further comprises assembling the plurality of images into a three dimensional model of the branched structure.

6. The method of claim 1 wherein imaging at least one tracing element attached to a device in the branched structure using a second imaging modality comprises imaging at least one radiopaque portion of the device.

7. The method of claim 6 wherein imaging at least one radiopaque portion of the device comprises imaging at least one radiopaque portion of the device using a fluoroscope.

8. The method of claim 1 wherein registering at least one image from the first imaging modality to at least one image from the second imaging modality comprises aligning anatomical features visible in the at least one image from the first imaging modality with corresponding anatomical features visible in the at least one image from the second imaging modality.

9. The method of claim 1 wherein registering at least one image from the first imaging modality to at least one image from the second imaging modality comprises aligning markers visible in the at least one image from the first imaging modality with corresponding markers visible in the at least one image from the second imaging modality.

10. The method of claim 1 wherein superimposing the at least one image from the first imaging modality and the at least one image from the second imaging modality comprises superimposing a fluoroscopic image onto a CT scan.

11. The method of claim 1 wherein navigating the device through the branched structure by viewing a location of the device in a real-time image obtained with the second imaging modality of the tracing element relative to the at least one image from the first imaging modality comprises viewing the at least one tracing element on a real-time fluoroscopic image superimposed over a CT scan while advancing the device.

* * * * *